US012582543B2

(12) United States Patent
Anstey et al.

(10) Patent No.: US 12,582,543 B2
(45) Date of Patent: Mar. 24, 2026

(54) APPARATUS FOR MOBILISING THE ANKLE JOINT

(71) Applicant: Azzurro Training Ltd, Beaconsfield (GB)

(72) Inventors: Matthew Anstey, Beaconsfield (GB); James Anstey, Beaconsfield (GB)

(73) Assignee: Azzurro Training Ltd, Beaconsfield (GB)

( * ) Notice: Subject to any disclaimer, the term of this patent is extended or adjusted under 35 U.S.C. 154(b) by 280 days.

(21) Appl. No.: 18/031,822

(22) PCT Filed: Oct. 6, 2021

(86) PCT No.: PCT/EP2021/077555
§ 371 (c)(1),
(2) Date: Apr. 13, 2023

(87) PCT Pub. No.: WO2022/078838
PCT Pub. Date: Apr. 21, 2022

(65) Prior Publication Data
US 2024/0016642 A1    Jan. 18, 2024

(30) Foreign Application Priority Data

Oct. 16, 2020    (GB) ..................................... 2016418

(51) Int. Cl.
*A61F 5/01*          (2006.01)
*A61H 1/02*          (2006.01)
(52) U.S. Cl.
CPC .......... *A61F 5/0111* (2013.01); *A61H 1/0266* (2013.01)
(58) Field of Classification Search
CPC .... A61F 5/0111; A61F 5/0127; A61F 5/0195; A61F 5/0113; A61F 5/04; A61F 5/042;
(Continued)

(56) References Cited

U.S. PATENT DOCUMENTS 3,847,147 A * 11/1974 Turner ..................... A43B 7/00
                                                  602/11
5,700,237 A * 12/1997 Hess ..................... A61F 5/0585
                                                  602/27
(Continued)

FOREIGN PATENT DOCUMENTS

JP        2005304658 A      11/2005
WO      2015/021684 A1      2/2015

OTHER PUBLICATIONS

International Search Report and Written Opinion issued for PCT/EP2021/077555, mailed Feb. 7, 2022.
Search Report issued for GB2016418.2, dated Mar. 18, 2021.

*Primary Examiner* — Keri J Nelson
(74) *Attorney, Agent, or Firm* — Westman, Champlin & Koehler, P.A.; Z. Peter Sawicki; Amanda M. Prose

(57)              ABSTRACT

Apparatus for mobilising a human ankle joint comprising a base (2) having an upper surface shaped to receive a foot with its heel adjacent the rear of the base and toes towards the front of the base, and a strap (4) extending from points adjacent the rear to form a loop extending towards the front, the loop being sufficiently long when a foot is in the base to pass around the ankle at the talo-crural joint, the left side of the upper surface having an upwardly-extending protrusion (PL) shaped to provide medial arch support to the arch of a right foot and the right side having a second upwardly-extending protrusion (PR) shaped to provide medial arch support to the arch of a left foot, the upper surface of the base between the protrusions being lower than the protrusions to support the foot's lateral edge, to resist inversion or eversion of the foot during dorsiflexion.

14 Claims, 2 Drawing Sheets

(58) Field of Classification Search
    CPC . A61F 5/048; A61H 1/0266; A61H 2201/164;
                A61H 2201/1642; A61H 2203/0406;
                    A43B 7/14; A63B 21/4013; A63B
                                                21/4015
    See application file for complete search history.

(56)                        References Cited

U.S. PATENT DOCUMENTS

| 6,206,807 B1 | 3/2001 | Cowans et al. |
| 6,361,514 B1 * | 3/2002 | Brown .................. A61F 5/0111 |
| | | 128/882 |
| 7,192,410 B1 | 3/2007 | Rodgers |
| 2006/0058719 A1 | 3/2006 | Nushart |
| 2015/0335460 A1 * | 11/2015 | Weaver, II ........... A43B 7/1464 |
| | | 602/7 |
| 2020/0206059 A1 * | 7/2020 | DeHeer ................... A61F 5/042 |

* cited by examiner

APPARATUS FOR MOBILISING THE ANKLE JOINT

CROSS-REFERENCE TO RELATED APPLICATION

This Application is a Section 371 National Stage Application of International Application No. PCT/EP2021/077555, filed Oct. 6, 2021 and published as WO/2022/078838 on Apr. 21, 2022, in English, which claims priority to GB patent application Serial No. 2016418.2, filed Oct. 16, 2020, the contents of which are hereby incorporated by reference in their entirety.

FIELD OF THE INVENTION

The present invention relates to apparatus for mobilising the ankle joint, in particular for facilitating and improving dorsiflexion of the human ankle.

BACKGROUND ART

Mobilising the ankle joint is a form of treatment or therapy used to improve the range of motion, alleviate pain and/or promote a return to function following injury; the technique is known as mobilisation with movement (MWM). Lateral ankle sprains, where the ankle undergoes excessive inversion and plantar flexion, are common among athletes and those walking or running on rough ground; such sprains result in reduced talocrural dorsiflexion and posterior glide of the talus in the ankle mortise, and these are believed in turn to create a predisposition to injury, stiffness, pain and reinjury, as well as increased chance of pain in other areas of the lower leg. Accordingly, imparting pressure during movement or manipulation of the ankle joint so as to facilitate anterior glide of the distal articular surface of the tibia over the talus and the posterior glide of the talus under the distal tibia is a mobilisation technique commonly used by physiotherapists and those treating patients with reduced dorsiflexion. The technique usually involves the manual application of pressure and controlled movement to the ankle joint, when the joint is either weight bearing (i.e. the subject is standing so that some at least of the subject's weight is applied through the joint) or non-weight-bearing; this requires a certain amount of skill and training on the part of the physiotherapist, and is not a technique which can easily be practised by the subject without the assistance of the therapist. This is disadvantageous because the patient would normally benefit by more frequent treatment than the therapist can provide in person; also, practising the technique over extended periods of time or on repeated patients can be tiring for the therapist.

Attempts have been made to develop suitable apparatus to exercise or mobilise the ankle joint which can be used with or without the therapist being present, such as the apparatus disclosed in US 2006/0058719 A1 or the ankle exercise device described in U.S. Pat. No. 6,206,807 B1, for example, but these conventional arrangements are complicated, bulky, expensive, may require skill or expertise to fit to a patient or may require the patient to learn how to use effectively and safely. In addition, many of the known ankle mobilisation devices apply forces to the ankle joint through the patient's foot, and they correctly consider how pressure is applied to the ankle joint, but they very often fail to consider the interaction of the skeletomuscular structure of the foot itself during ankle flexion—whilst the mobilisation of the ankle is the main objective this should not allow the foot to deform or to move in an unnatural or potentially unsafe manner. Lastly, many known devices are usable with either a left or right foot, but require adjustment before they can be used with the opposite foot. There is a need for apparatus which is simpler and more straightforward to make and use than conventional devices, which is preferably intuitive to use correctly, and which correctly supports and guides either foot during ankle mobilisation.

SUMMARY OF THE INVENTION

The present invention is predicated on using the weight of the standing patient to stabilise the talus and tarsal bones and, during movement of the ankle joint, to apply pressure to promote posterior glide of the talus under the distal tibia. Therefore the present invention provides an apparatus for mobilising a human ankle joint comprising: a one-piece base having front and rear ends, left and right sides and an upper surface which is shaped and configured to receive and support a foot with its heel adjacent the rear end and toes pointing towards the front end, and a strap extending from two spaced points adjacent the rear end to form a loop extending towards the front end, the loop being of sufficient length when a foot is received in and supported by the base to pass around the foot and ankle at the talo-crural joint, in which the left side of the upper surface has a first upwardly-extending protrusion shaped and configured to provide medial arch support to the arch of a right foot and the right side has a second upwardly-extending protrusion shaped and configured to provide medial arch support to the arch of a left foot, the upper surface of the base between the first and second protrusions being lower than the protrusions so as to support the lateral edge of a foot and shaped and configured, in combination with the first and second protrusions, to support the foot and resist inversion or eversion during dorsiflexion of the foot.

Such an arrangement is very easy to make and to use, and consists of two main components: an ergonomically designed, one-piece base that is sufficiently rigid to provide medial arch support for both left and right feet to prevent collapsing of the foot arch during the dorsiflexion (arch collapse is a common compensatory mechanism during mobilisation into dorsiflexion), with a common, shared centre platform that supports and prevents the lateral border of the foot from moving laterally, and a strap that attaches to the base, behind the heel, and travels diagonally and forwardly over the bridge of the foot at the ankle joint to apply pressure and provide support to the talus and tarsal bones during dorsiflexion. When positioned correctly the strap supports both the Talus and Tarsal bones by sitting on the anterior, superior portion of the Talus and, when secured, provides downward and posterior pressure on the Talo-Crural joint to promote posterior and inferior glide of the joint. The apparatus is intuitive to use, and requires the user simply to rest a foot to one or other side of the base (because of the ergonomic shape of the upper surface of the base, the user will naturally place the foot in the position where the foot is comfortably supported by the base), to position the strap correctly on the front part of the ankle (which position the patient need only be shown once by the therapist), and then to apply some weight to the foot in the apparatus and lean that leg forwardly so as to move the ankle in dorsiflexion as far as is comfortable. The patient may hold the ankle in dorsiflexion for a time, relax, and then repeat the exercise.

The strap is flexible and preferably inelastic and adjustable to vary the length of the loop, so that the apparatus can be easily adapted for use by subjects having differently-sized feet and ankles, or to accommodate dorsiflexion at greater angles, so the same apparatus is suitable for the great majority of adult patients (the limiting factor as to the range of sizes of feet/legs which can be accommodated being determined more by the ergonomic base shape than the range of strap adjustment). The strap may have a sliding buckle and/or may be provided with hook-and-loop fasteners so as to allow the length of the loop to be adjusted easily.

The upper surface of the base may be provided with at least one cup for receiving and supporting a heel, the or each cup being located towards but spaced forwardly from the rear end of the base. This makes a comfortable and intuitive position for the user to place the heel. Preferably the or each cup is located to receive and support the rear of the heel forwardly of the two points adjacent the rear end from which the strap extends. This ensures that when the user flexes the ankle joint the strap applies pressure to the joint at the correct position and in the correct direction to promote posterior glide. The cup may be in the form of a single concave depression more or less centrally-located between the left and right sides of the base, so that the heel always rests in the same spot regardless of whether a right foot or a left foot is to be placed on the base, with the foot swivelling on the heel to the left or to the right as appropriate, or the cup can be shaped and configured to receive and support a right heel towards the left side of the base and a left heel towards the right side of the base. In the latter case, when the user places a foot in the apparatus the foot is positioned so that the heel is located towards the left or right side of the base, on the same side at which the relevant protrusion is supporting the user's arch. There may be two cups or concave depressions, one on either side at the rear of the base, to receive and support either a left or a right heel.

The two points from which the strap extends may be spaced laterally by a distance greater than the width of the average human heel, and preferably outside the or each cup. This allows a foot to be placed on the base and inside the loop easily, and for the used to slide the heel to left or right where applicable. It is also important for the correct application of pressure in use. The strap has a width transverse to its length, and is preferably arranged such that, at the two points from which it extends, the width of the strap is at an acute forward angle with the axis extending from the rear end to the front end of the base. This is necessary to ensure that, with the strap extended around the ankle in use, it conforms to the surface of the ankle (and hence is not uncomfortable in use) and it applies pressure evenly over the talus and tarsal bones and in the desired direction.

The base may be formed of a rigid material, such as injection moulded plastic, wood or composite material, and/or it may comprise an upper surface formed of a resilient cushioning material. Such a cushioning material conforms to the shape of the foot and so is comfortable in use, but it needs to be sufficiently springy to provide adequate and effective support to the medial arch. The material is suitably waterproof and/or cleanable, for hygienic purposes, particularly if the same apparatus is to be used by different patients. The upper surface between the first and second protrusions preferably forms a smoothly contoured roll surface, with a maximum height above the base plane towards the left and right sides of the base and a minimum height above the plane of the base towards the lateral centre. This not only makes for comfort and for intuitive positioning of a foot by a user, it also presents an aesthetically pleasing appearance.

BRIEF DESCRIPTION OF THE DRAWINGS

The invention will now be described by way of example and with reference to the accompanying figures, in which;

FIG. 3a is a plan view of the apparatus of FIG. 1;

FIG. 3b is a rear elevation view of the apparatus of FIG. 1;

FIG. 3c is a cross-sectional view along Lines AA in FIG. 3a, and

FIG. 3d is a view from the underside of the apparatus of FIG. 1.

DETAILED DESCRIPTION OF THE EMBODIMENTS

Figures 1A, 1B, 1C, 2A, 2B:
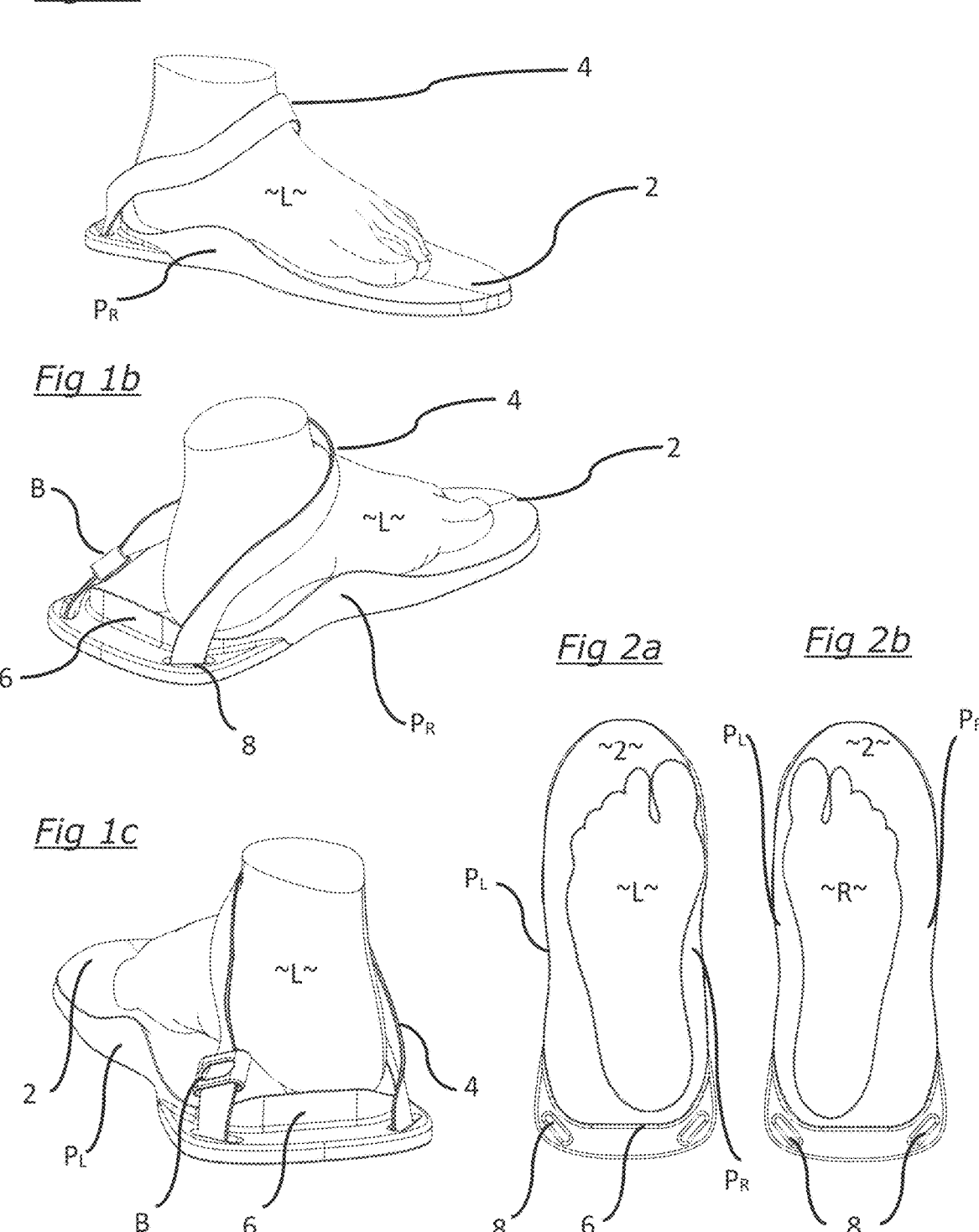
FIGS. 1a, 1b and 1c are schematic perspective views of an embodiment of the present invention in use.
FIGS. 2a and 2b are schematic plan views of the apparatus of FIG. 1 illustrating the positioning of, respectively, a right foot and a left foot in the apparatus.

FIGS. 1a, 1b and 1c show a left foot L resting on a base 2 and a strap 4 extending in a loop from the rear of the base and passing over the foot L adjacent the ankle. The base is shaped so as to have two upstanding protrusions $P_R$ on the right hand side of the base and $P_L$ on the left hand side of the base (see FIG. 2a); these protrusions provide support to the medial arch of the foot. The base 2 is also provided with a laterally-extending, upstanding lip 6 dimensioned so as to provide a stop for locating the heel of the foot in the front/rear direction relative to the base 2; this lip 6 acts as a "cup" for the user to position the heel correctly on the base 2 so that the strap 4 passes over the foot in the desired position (at the Talo-Crural joint) and orientation. The strap has a buckle B so that its length may be adjusted, so that the strap 4 is in the correct position for feet/ankles of varying sizes. The buckle, in combination with conventional hook-and-loop fastener patches (not shown), allows the strap 2 to be looped and secured tightly over the foot, and to apply downward inferior pressure through the Talo-Crural joint so as to promote the required gliding movement of the joint. The strap 2 is flexible and inelastic, formed of nylon, and the buckle is rigid and robust, formed of metal or plastic and sewn or otherwise secured to an end of the strap. The base is sturdy and robust, and here is made of injection-moulded thermoplastic (ABS) as an integral, or one-piece, item; the base may have structural reinforcements to prevent the base from deforming under load. The lower surface of the base may be divided into separate recesses by a grid of projecting ribs; this provides structural strength whilst reducing the amount of material in, and the weight of, the base, it also aids the injection moulding process. This grid may also help to make the base grip the floor underneath; additionally or alternatively a layer of material may be applied to the lower surface of the base to increase the friction between the base and the floor underneath, for example the layer may have a "treaded" or rough pattern, or be formed of a material with a high coefficient of friction.

FIGS. 2a and 2b illustrate how a user locates the left foot L or right foot R upon the base 2 for use with the apparatus. In FIG. 2a the left foot L is positioned so that the heel is adjacent the right hand edge of the base with the heel touching the lip 6, and the arch of the foot is located over the right hand protrusion $P_R$. In FIG. 2b, the right foot R is positioned so that the heel is adjacent the left hand edge of the base with the heel touching the lip 6, and the arch of the foot is located over the left hand protrusion $P_L$.

Figures 3A, 3B, 3C, 3D:
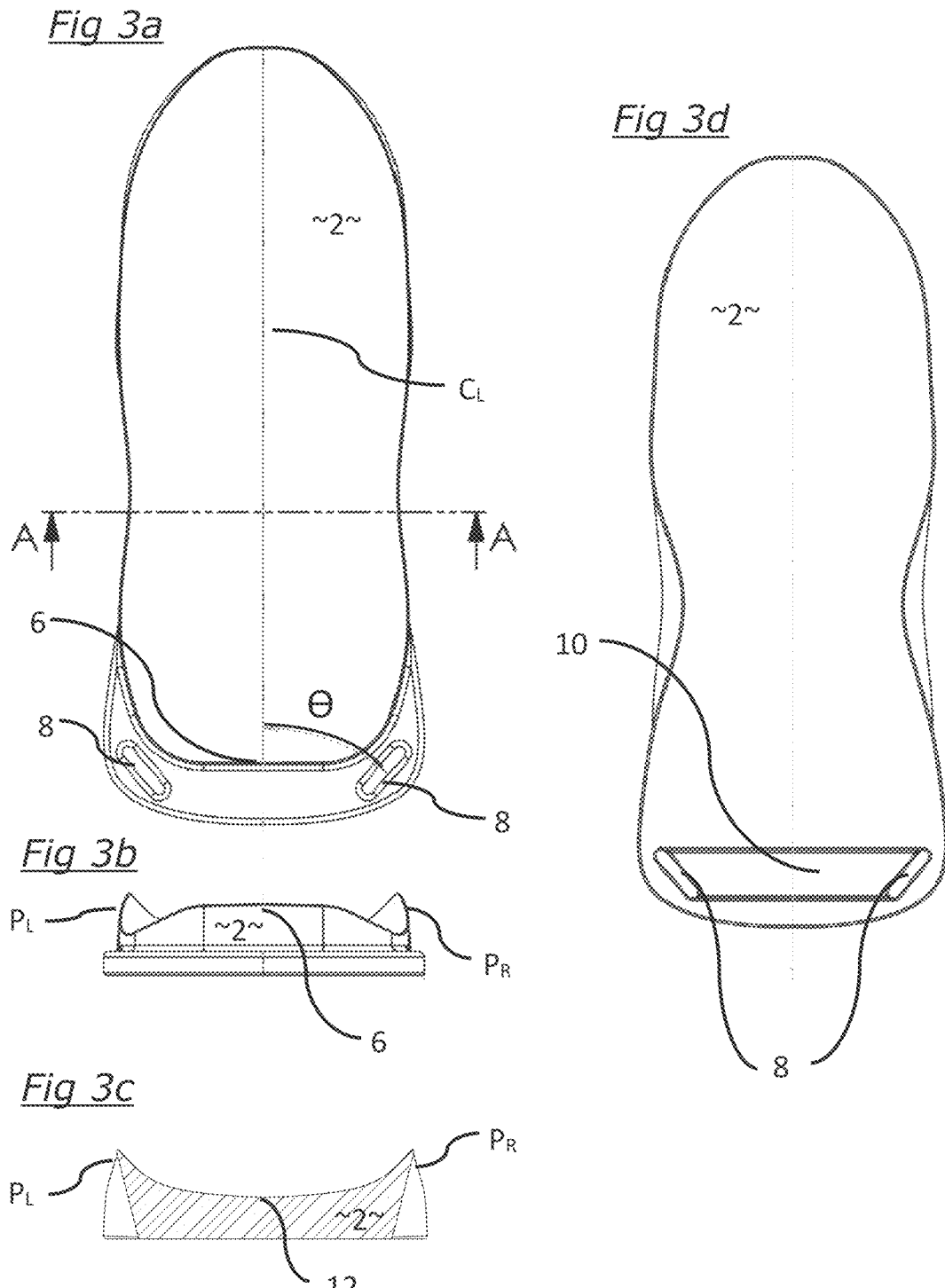

FIG. 3a shows the base 2 in plan view without the strap. Two holes 8 are provided in the base, either side of the centre line $C_L$ of the base 2 for the strap to pass through. As can be seen in the view from below in FIG. 3d, there is a recess 10 in the bottom of the base 2 for the strap to sit in and extend between the two holes 8; this recess 10 prevents the strap from being abraded by contact with the floor when the apparatus is in use. This allows the strap to be movable lengthwise relative to the base, so as to position the buckle in a comfortable or convenient position for example. The location and orientation of the holes is very important for the apparatus to operate effectively, because the holes to a large extent dictate the orientation of the strap as it passes over the foot, and the positioning of the strap relative to the Talo-Crural joint. We have found that for the apparatus of FIG. 1, with a strap of width 20-25 mm, the holes 8 should be located about 5-10 mm behind the lip 6 (or the rearmost part of the heel), equally spaced laterally about 50-60 mm from the centre line $C_L$ and at an angle $\Theta$ of about 40° (+/−5°) to the centre line $C_L$. The other important dimension is the height of the protrusions $P_L$, $P_R$; we have found that a maximum height of 20-40 mm above the lowest part 12 of the upper surface of the base 2 provides good medial arch support. Other dimensions of the apparatus are of lesser significance, a base length of 300-350 mm, width of 100-150 mm will accommodate most adult feet, alternative dimensions may be more suitable for particularly small (i.e. children's) feet or extremely large feet.

As can be seen in FIGS. 3b and 3c, the left and right protrusions $P_L$, $P_R$ are located towards the left and right sides of the base; between these protrusions the upper surface of the base curves smoothly down, following the lateral shape of the typical foot, to a low 12 which extends laterally. In use, when a foot is located with the arch being supported by a protrusion, the lateral border (outer edge) of the foot locates on this low 12 and the gradual curve up to the protrusion on the opposite side helps prevent unwanted lateral movement of the foot. The lateral extent of the low 12 also helps accommodate feet of differing widths comfortably. It will be appreciated from FIG. 3b that the tops of the holes 8 are at approximately the same level as the bottom of the cup 8, so that the tops of the holes would be at about the same level as the heel of a user resting inside the cup.

The apparatus is used in the following manner:

1. Rest the right foot on the left-side of the base, ensuring the heel is supported by the raised lip at the rear and the arch of the foot is supported by the raised arch of the base.
2. Loop the strap over and around the top of the foot/ankle, ensuring the strap is positioned correctly at the Talo-Crural joint, and through the buckle on the other side. Secure tightly, but comfortably, using the buckle and hook-and-loop fastener to secure the strap.
3. Perform 10 weight-bearing ankle dorsiflexion bending movements over approximately 30 seconds (knee over foot method), whilst the left foot helps maintain balance whilst performing this movement.
4. Once complete, unstrap the right foot and repeat steps 1-3 but for the left foot placed on the right-side of the base.

It will of course be understood that many variations may be made to the above-described embodiment without departing from the scope of the present invention. For example, a soft, flexible and/or elastic padding material could be secured to the inside of the loop to lie against the skin to provide extra comfort, such as neoprene or Lycra (a registered trade mark of the Lycra Company). Other fastening methods could be used on the strap, such as a ladder strap or a lashing strap. The drawings show a laterally-extending lip forming a rear stop for the heel, however this lip could be curved so as to form a concave cup shape; in this case, the cup would be located centrally on the base relative to the centreline so that either heel would sit in the same position on the base but the foot would pivot left or right so that the arch is located comfortably over the appropriate protrusion. The base is illustrated as being unitary, formed of a single material, but it could comprise a rigid base part with an upper surface part formed of a suitable cushioning material. The "stepped" appearance of the rear part of the base where the holes 8 are located and the rear of the cup 6, as shown in FIG. 1b, could be modified so as to have a smoothly curved and more aesthetically-appealing appearance. The inner surfaces of the holes 8 are shown in the drawings as being vertically aligned, however the holes, or possibly only the innermost long surfaces of the holes, could be slanted inwardly towards the centre line $C_L$; this would facilitate the strap 4 being moved along the recess 10 and relative to the base 2, which might be needed when adjusting the strap to fit a user with a differently sized foot than the previous user, for example, to ensure the strap lies accurately over the talo-crural joint, or to locate the buckle B where desired.

Where different variations or alternative arrangements are described above, it should be understood that embodiments of the invention may incorporate such variations and/or alternatives in any suitable combination.

The invention claimed is:

1. An apparatus for mobilising a human ankle joint comprising:

a base part having an upper surface with front and rear ends, and left and right sides, the upper surface being shaped and configured to receive and support a foot with its heel adjacent the rear end and toes pointing towards the front end, and a strap extending from two points adjacent the rear end to form a loop extending towards the front end, the loop being of sufficient length when a foot is received in and supported by the base part to pass around the foot and ankle at the talo-crural joint, in which the left side of the upper surface has a first upwardly-extending protrusion shaped and configured to provide medial arch support to the arch of a right foot when the arch of the right foot is positioned over the first protrusion and the right side has a second upwardly-extending protrusion shaped and configured to provide medial arch support to the arch of a left foot when the arch of the left foot is positioned over the second protrusion, the upper surface of the base part between the first and second protrusions being lower than the protrusions so as to support the lateral edge of a foot and to prevent lateral movement of the foot when the outer lateral edge of the foot is located on a lower part of the upper surface of the base part between the first and second protrusions and shaped and configured, in combination with the first and second protrusions, to support the foot and resist inversion or eversion during dorsiflexion of the foot.

2. The apparatus as claimed in claim 1, further comprising at least one cup for receiving and supporting a heel, the at least one cup being located towards but spaced from the rear end of the base part.

3. The apparatus as claimed in claim 2, in which the at least one cup is located to receive and support the rear of the heel forwardly of the two points adjacent the rear end from which the strap extends.

4. The apparatus as claimed in claim 1, in which a first cup is shaped and configured to receive and support a right heel towards the left side of the base part and a second cup is shaped and configured to receive and support a left heel towards the right side of the base part.

5. The apparatus as claimed in claim 1, in which a single cup is shaped and configured to receive and support a heel substantially centrally between the left and right sides of the base part.

6. The apparatus as claimed in claim 1, in which the strap is flexible and/or inelastic.

7. The apparatus as claimed in claim 1, in which the two points from which the strap extends are spaced laterally by a distance greater than the width of the average human heel.

8. The apparatus as claimed in claim 1, in which the strap has a width transverse to its length, and is arranged such that, at the two points from which it extends, the width of the strap is at an acute forward angle with the axis extending from the rear end to the front end of the base part.

9. The apparatus as claimed in claim 1, in which the length of the strap is variable.

10. The apparatus as claimed in claim 1, in which the base part is formed of a rigid material.

11. The apparatus as claimed in claim 1, in which the upper surface of the base part is formed of a resilient cushioning material.

12. The apparatus according to claim 1, in which the upper surface between the first and second protrusions forms a smoothly contoured roll surface.

13. The apparatus according to claim 1, further comprising a frictional layer provided on a lower surface of the base part.

14. The apparatus according to claim 1, in which the two points from which the strap extends are holes extending through the rear end of the base part, a recess being provided on the lower surface of the base part and extending between lower ends of the holes for a lower part of the strap to lie along in use.

* * * * *